United States Patent
Ingimundarson et al.

(10) Patent No.: US 9,439,800 B2
(45) Date of Patent: Sep. 13, 2016

(54) ORTHOPEDIC DEVICE, USE OF ORTHOPEDIC DEVICE AND METHOD FOR PRODUCING SAME

(75) Inventors: Arni Thor Ingimundarson, Gardabaer (IS); Thorvaldur Ingvarsson, Akureyri (IS); Nina Bakken, Oslo (NO); Chad Leeder, Orrville, OH (US)

(73) Assignee: OSSUR HF, Reykjavik (IS)

( * ) Notice: Subject to any disclaimer, the term of this patent is extended or adjusted under 35 U.S.C. 154(b) by 405 days.

(21) Appl. No.: 13/528,032

(22) Filed: Jun. 20, 2012

(65) Prior Publication Data
US 2012/0323154 A1 Dec. 20, 2012

Related U.S. Application Data

(60) Provisional application No. 61/498,831, filed on Jun. 20, 2011.

(51) Int. Cl.
*A61F 5/01* (2006.01)
*A61F 5/32* (2006.01)

(52) U.S. Cl.
CPC .............. *A61F 5/0193* (2013.01); *A61F 5/01* (2013.01); *A61F 5/32* (2013.01); *A61F 2005/0158* (2013.01)

(58) Field of Classification Search
CPC .. A61F 5/0123; A61F 5/0125; A61F 5/0193; A61F 2005/0134; A61F 5/01; A61F 5/32; A61F 2005/0158
USPC ........ 602/5, 6, 8, 10, 16, 20, 23–29, 62, 63, 602/19; 128/105.1, 878, 879, 882; 623/28, 623/30, 31; 2/22, 24
See application file for complete search history.

(56) References Cited

U.S. PATENT DOCUMENTS

| 7,916 A | 1/1851 | Knapp |
| 61,487 A | 1/1867 | Vollschwitz |

(Continued)

FOREIGN PATENT DOCUMENTS

| AU | 2010271020 A1 | 2/2012 |
| AU | 2010271020 A2 | 2/2012 |

(Continued)

OTHER PUBLICATIONS

International Search Report and Written Opinion of the International Searching Authority issued in PCT/US2012/043252, Jan. 10, 2013.

(Continued)

*Primary Examiner* — Kari Petrik
(74) *Attorney, Agent, or Firm* — Workman Nydegger

(57) ABSTRACT

An orthopedic device includes an elongate and rigid or semirigid strut assembly, an arcuate cuff pivotally secured to the strut assembly, and a strap securing to the cuff and forming an adjustable circumferential configuration therewith. A tensioning device may be mounted on the cuff and coupled to the strap in order to incrementally adjust the tensioning device among a plurality of preselected levels such that a first end of the strap secures to the tensioning device and a second end of the strap couples to the cuff. A soft-good assembly connects to the strut assembly and has a flexible stay embedded within with a plurality of layers. The soft-good assembly is adapted to form an adjustable circumferential loop with the stay only located within a segment short of the circumference of the loop.

4 Claims, 7 Drawing Sheets

(56) References Cited

U.S. PATENT DOCUMENTS

| | | |
|---|---|---|
| 181,948 A | 9/1876 | Kleinschuster |
| 232,420 A | 9/1880 | Smith |
| 321,145 A | 6/1885 | Spencer |
| 321,146 A | 6/1885 | Spencer |
| 328,638 A | 10/1885 | Battershall |
| 368,699 A | 8/1887 | Zervas |
| 386,642 A | 7/1888 | Mann |
| 596,849 A | 1/1889 | Combier |
| 507,172 A | 10/1893 | Shelden |
| 571,749 A | 11/1896 | Colton |
| 601,446 A | 3/1898 | Mestler |
| 616,196 A | 12/1898 | Medbury |
| 629,900 A | 8/1899 | Fosburgh |
| 639,072 A | 12/1899 | Lyons |
| 664,250 A | 12/1900 | Fitzpatrick |
| 709,055 A | 9/1902 | Sheldon |
| 714,124 A | 11/1902 | Adams |
| 746,563 A | 12/1903 | McMahon |
| 772,926 A | 10/1904 | Colton |
| 787,894 A | 4/1905 | Colton |
| 888,490 A | 5/1908 | Haas |
| 894,066 A | 7/1908 | Scapra |
| 980,457 A | 1/1911 | Toles |
| 1,124,596 A | 1/1915 | Dalpe |
| 1,316,915 A | 9/1919 | Meyer et al. |
| 1,393,188 A | 10/1921 | Whitman |
| 1,463,579 A | 7/1923 | Funck |
| 1,469,661 A | 10/1923 | Migita |
| 1,481,903 A | 1/1924 | Hart |
| 1,530,713 A | 3/1925 | Clark |
| 1,558,661 A | 10/1925 | Yeganian |
| 1,755,641 A | 4/1930 | Foulke |
| 1,948,785 A | 2/1934 | Dondelinger |
| 1,981,157 A | 11/1934 | Walter |
| 2,036,484 A | 4/1936 | Le May |
| 2,100,964 A | 11/1937 | Kendrick |
| 2,117,309 A | 5/1938 | Fritsch |
| 2,219,475 A | 10/1940 | Flaherty |
| 2,409,381 A | 10/1946 | Pease, Jr. |
| 2,543,370 A | 11/1948 | Hittenberger |
| 2,554,337 A | 5/1951 | Lampert |
| 2,630,801 A | 3/1953 | Mest et al. |
| 2,696,011 A | 12/1954 | Galdik |
| 2,749,550 A | 6/1956 | Pease |
| 2,793,368 A | 5/1957 | Nouel |
| 2,808,050 A | 10/1957 | Ward |
| 2,815,021 A | 12/1957 | Freeman |
| 2,828,737 A | 4/1958 | Hale |
| 2,904,040 A | 9/1959 | Hale |
| 2,906,260 A | 9/1959 | Myers |
| 2,906,261 A | 9/1959 | Craig |
| 3,095,875 A | 7/1963 | Davidson et al. |
| 3,096,760 A | 7/1963 | Nelkin |
| 3,218,514 A | 11/1965 | Parker et al. |
| 3,274,996 A | 9/1966 | Jewett |
| 3,282,264 A | 11/1966 | Connelly |
| 3,351,053 A | 11/1967 | Stuttle |
| 3,371,351 A | 3/1968 | Allain |
| 3,434,469 A | 3/1969 | Swift |
| 3,480,012 A | 11/1969 | Smithers et al. |
| 3,509,875 A | 5/1970 | Richter |
| 3,548,817 A | 12/1970 | Mittasch |
| 3,563,431 A | 2/1971 | Pletz |
| 3,570,480 A | 3/1971 | Stubbs |
| 3,578,773 A | 5/1971 | Schultz |
| 3,600,717 A | 8/1971 | McKeehan |
| 3,601,819 A | 8/1971 | Herrmann |
| 3,762,421 A | 10/1973 | Sax, Sr. |
| 3,771,513 A | 11/1973 | Velazquez |
| 3,793,749 A | 2/1974 | Gertsch et al. |
| 3,808,644 A | 5/1974 | Schoch |
| 3,812,850 A | 5/1974 | Reiman |
| 3,816,211 A | 6/1974 | Haigh |
| 3,834,048 A | 9/1974 | Maurer |
| 3,889,664 A | 6/1975 | Heuser et al. |
| 3,902,503 A | 9/1975 | Gaylord, Jr. |
| 3,920,008 A | 11/1975 | Lehman |
| 3,926,182 A | 12/1975 | Stabbolz |
| 3,927,665 A | 12/1975 | Wax |
| 3,945,376 A | 3/1976 | Kuehnegger |
| 4,042,433 A | 8/1977 | Hardy et al. |
| 4,055,168 A | 10/1977 | Miller et al. |
| 4,071,387 A | 1/1978 | Schlaepfer |
| 4,099,524 A | 7/1978 | Cueman et al. |
| 4,114,788 A | 9/1978 | Zufich |
| 4,173,973 A | 11/1979 | Hendricks |
| 4,175,553 A | 11/1979 | Rosenberg |
| 4,230,101 A | 10/1980 | Gold |
| 4,261,081 A | 4/1981 | Lott |
| 4,285,336 A | 8/1981 | Oebser et al. |
| 4,383,523 A | 5/1983 | Schurman |
| 4,392,489 A | 7/1983 | Wagner, Sr. |
| 4,433,456 A | 2/1984 | Baggio |
| RE31,564 E | 4/1984 | Hendricks |
| 4,475,543 A | 10/1984 | Brooks et al. |
| 4,494,536 A | 1/1985 | Latenser |
| 4,502,471 A | 3/1985 | Owens |
| 4,508,110 A | 4/1985 | Modglin |
| 4,555,830 A | 12/1985 | Petrini et al. |
| 4,559,933 A | 12/1985 | Batard et al. |
| 4,569,336 A | 2/1986 | Wheeler |
| 4,574,500 A | 3/1986 | Aldinio et al. |
| 4,574,789 A | 3/1986 | Forster |
| 4,574,790 A * | 3/1986 | Wellershaus .................. 602/24 |
| 4,608,971 A | 9/1986 | Borschneck |
| 4,616,524 A | 10/1986 | Bidoia |
| 4,619,657 A | 10/1986 | Keates et al. |
| 4,628,913 A | 12/1986 | Lerman |
| 4,631,839 A | 12/1986 | Bonetti et al. |
| 4,631,840 A | 12/1986 | Gamm |
| 4,635,626 A | 1/1987 | Lerman |
| 4,640,269 A | 2/1987 | Goins |
| 4,648,390 A | 3/1987 | Friddle |
| 4,649,574 A | 3/1987 | Michels |
| 4,654,985 A | 4/1987 | Chalmers |
| 4,658,807 A | 4/1987 | Swain |
| 4,660,302 A | 4/1987 | Arieh et al. |
| 4,677,699 A | 7/1987 | Barabe |
| 4,680,878 A | 7/1987 | Pozzobon et al. |
| 4,691,696 A | 9/1987 | Farfan de los Godos |
| 4,696,291 A | 9/1987 | Tyo |
| 4,697,592 A | 10/1987 | Maddux et al. |
| 4,719,670 A | 1/1988 | Kurt |
| 4,719,709 A | 1/1988 | Vaccari |
| 4,761,834 A | 8/1988 | Kolb |
| 4,796,610 A * | 1/1989 | Cromartie .................. 602/26 |
| 4,799,297 A | 1/1989 | Baggio et al. |
| 4,802,291 A | 2/1989 | Sartor |
| 4,805,605 A | 2/1989 | Glassman |
| 4,807,605 A | 2/1989 | Mattingly |
| 4,811,503 A | 3/1989 | Iwama |
| 4,843,688 A | 7/1989 | Ikeda |
| 4,862,878 A | 9/1989 | Davison et al. |
| 4,870,761 A | 10/1989 | Tracy |
| 4,905,678 A * | 3/1990 | Cumins et al. .................. 602/16 |
| 4,923,474 A | 5/1990 | Klasson et al. |
| 4,937,952 A | 7/1990 | Olivieri |
| 4,961,544 A | 10/1990 | Bidoia |
| 4,963,208 A | 10/1990 | Muncy et al. |
| 4,976,257 A | 12/1990 | Akin et al. |
| 5,027,482 A | 7/1991 | Torppey |
| 5,072,725 A | 12/1991 | Miller |
| 5,074,288 A | 12/1991 | Miller |
| 5,092,321 A | 3/1992 | Spademan |
| 5,098,770 A | 3/1992 | Paire |
| 5,105,828 A | 4/1992 | Grant |
| 5,111,807 A | 5/1992 | Spahn et al. |
| 5,117,567 A | 6/1992 | Berger |
| 5,120,288 A | 6/1992 | Sinaki |
| 5,121,741 A | 6/1992 | Bremer et al. |
| 5,127,897 A | 7/1992 | Roller |
| 5,135,470 A | 8/1992 | Reeves |
| 5,135,471 A | 8/1992 | Houswerth |
| 5,154,690 A | 10/1992 | Shiono |

(56) References Cited

U.S. PATENT DOCUMENTS

| | | |
|---|---|---|
| 5,157,813 A | 10/1992 | Carroll |
| 5,170,505 A | 12/1992 | Rohrer |
| 5,171,296 A | 12/1992 | Herman |
| 5,176,131 A | 1/1993 | Votel et al. |
| 5,177,882 A | 1/1993 | Berger |
| 5,181,331 A | 1/1993 | Berger |
| 5,183,036 A | 2/1993 | Spademan |
| D334,063 S | 3/1993 | DeWall |
| 5,199,940 A | 4/1993 | Morris et al. |
| 5,201,074 A | 4/1993 | Dicker |
| 5,203,765 A | 4/1993 | Friddle, Jr. |
| 5,215,518 A | 6/1993 | Rosen |
| 5,226,874 A | 7/1993 | Heinz et al. |
| 5,230,698 A | 7/1993 | Garth |
| 5,259,831 A | 11/1993 | LeBron |
| 5,259,833 A | 11/1993 | Barnett |
| 5,295,947 A | 3/1994 | Muncy |
| 5,307,521 A | 5/1994 | Davis |
| 5,313,952 A | 5/1994 | Hoch |
| 5,318,575 A | 6/1994 | Chesterfield et al. |
| 5,327,662 A | 7/1994 | Hallenbeck |
| 5,334,135 A | 8/1994 | Grim et al. |
| 5,342,289 A | 8/1994 | Munny |
| 5,346,461 A | 9/1994 | Heinz et al. |
| 5,363,863 A | 11/1994 | Lelli et al. |
| 5,365,947 A | 11/1994 | Bonutti |
| 5,368,552 A | 11/1994 | Williamson et al. |
| 5,376,129 A | 12/1994 | Faulkner et al. |
| 5,383,893 A | 1/1995 | Daneshvar |
| 5,387,245 A | 2/1995 | Fay et al. |
| 5,399,151 A | 3/1995 | Smith |
| 5,421,809 A | 6/1995 | Rise |
| 5,423,852 A | 6/1995 | Daneshvar |
| 5,429,587 A | 7/1995 | Gates |
| 5,433,648 A | 7/1995 | Frydman |
| 5,433,697 A | 7/1995 | Cox |
| 5,435,015 A | 7/1995 | Ellis-Brewer |
| 5,437,614 A | 8/1995 | Grim |
| 5,437,617 A | 8/1995 | Heinz et al. |
| 5,437,619 A | 8/1995 | Malewicz et al. |
| 5,449,338 A | 9/1995 | Trudell |
| 5,450,858 A | 9/1995 | Zablotsky et al. |
| 5,466,214 A | 11/1995 | Calderon-Garciduenas |
| 5,484,395 A | 1/1996 | DeRoche |
| 5,499,965 A | 3/1996 | Sanchez |
| 5,500,959 A | 3/1996 | Yewer, Jr. |
| 5,502,902 A | 4/1996 | Sussmann |
| 5,503,314 A | 4/1996 | Fiscus |
| 5,503,620 A | 4/1996 | Danzger |
| 5,507,681 A | 4/1996 | Smith et al. |
| 5,507,834 A | 4/1996 | Laghi |
| 5,520,619 A | 5/1996 | Martin |
| 5,522,792 A | 6/1996 | Bassett et al. |
| 5,531,669 A | 7/1996 | Varnau |
| 5,536,246 A | 7/1996 | Saunders |
| 5,539,020 A | 7/1996 | Bracken et al. |
| 5,548,843 A | 8/1996 | Chase et al. |
| 5,551,950 A | 9/1996 | Oppen |
| 5,558,628 A | 9/1996 | Bzoch |
| 5,569,171 A | 10/1996 | Muncy |
| 5,571,355 A | 11/1996 | Kornylo |
| 5,599,287 A | 2/1997 | Beczak, Sr. et al. |
| 5,599,288 A | 2/1997 | Shirley et al. |
| 5,603,122 A | 2/1997 | Kania |
| 5,620,412 A | 4/1997 | Modglin |
| 5,622,529 A | 4/1997 | Calabrese |
| 5,632,724 A | 5/1997 | Lerman et al. |
| 5,634,891 A | 6/1997 | Beczak, Sr. et al. |
| 5,638,588 A | 6/1997 | Jungkind |
| 5,669,116 A | 9/1997 | Jungkind |
| 5,674,187 A | 10/1997 | Zepf |
| 5,681,270 A | 10/1997 | Klearman et al. |
| 5,685,830 A | 11/1997 | Bonutti |
| 5,685,831 A | 11/1997 | Floyd |
| 5,688,137 A | 11/1997 | Bustance |
| 5,690,260 A | 11/1997 | Aikins et al. |
| 5,690,609 A | 11/1997 | Heinze, III |
| 5,695,452 A | 12/1997 | Grim et al. |
| 5,704,904 A | 1/1998 | Dunfee |
| 5,704,937 A | 1/1998 | Martin |
| 5,708,977 A | 1/1998 | Morkunas |
| 5,718,670 A | 2/1998 | Bremer |
| 5,722,940 A | 3/1998 | Gaylord, Jr. et al. |
| 5,724,993 A | 3/1998 | Dunfee |
| 5,725,139 A | 3/1998 | Smith |
| 5,728,054 A | 3/1998 | Martin |
| 5,728,168 A | 3/1998 | Laghi et al. |
| 5,732,483 A | 3/1998 | Cagliari |
| 5,737,854 A | 4/1998 | Sussmann |
| 5,746,218 A | 5/1998 | Edge |
| 5,752,640 A | 5/1998 | Proulx |
| 5,778,565 A | 7/1998 | Holt et al. |
| 5,782,782 A | 7/1998 | Miller |
| 5,795,316 A | 8/1998 | Gaylord |
| RE35,940 E | 10/1998 | Heinz et al. |
| 5,816,251 A | 10/1998 | Glisan |
| 5,819,378 A | 10/1998 | Doyle |
| 5,823,981 A | 10/1998 | Grim et al. |
| 5,826,766 A | 10/1998 | Aftanas |
| 5,827,211 A | 10/1998 | Sellinger |
| 5,830,167 A | 11/1998 | Jung |
| 5,836,493 A | 11/1998 | Grunsted et al. |
| 5,840,050 A | 11/1998 | Lerman |
| 5,848,979 A | 12/1998 | Bonutti et al. |
| 5,853,378 A | 12/1998 | Modglin |
| 5,853,379 A | 12/1998 | Ostojic |
| 5,857,988 A | 1/1999 | Shirley |
| 5,868,292 A | 2/1999 | Stephens et al. |
| 5,890,640 A | 4/1999 | Thompson |
| 5,891,061 A | 4/1999 | Kaiser |
| 5,911,697 A | 6/1999 | Biedermann et al. |
| 5,916,070 A | 6/1999 | Donohue |
| 5,938,629 A | 8/1999 | Bloedau |
| 5,950,628 A | 9/1999 | Dunfee |
| 5,954,250 A | 9/1999 | Hall et al. |
| 5,954,253 A | 9/1999 | Swetish |
| 5,967,998 A | 10/1999 | Modglin |
| 5,993,403 A | 11/1999 | Martin |
| 6,010,472 A | 1/2000 | Schiller |
| 6,027,466 A | 2/2000 | Diefenbacher et al. |
| 6,029,273 A | 2/2000 | McCrane |
| 6,036,664 A | 3/2000 | Martin, Sr. et al. |
| 6,039,707 A | 3/2000 | Crawford et al. |
| 6,063,047 A | 5/2000 | Minne |
| 6,066,108 A | 5/2000 | Lundberg |
| 6,070,776 A | 6/2000 | Furnary et al. |
| 6,090,057 A | 7/2000 | Collins et al. |
| 6,099,490 A | 8/2000 | Turtzo |
| 6,110,138 A | 8/2000 | Shirley |
| 6,117,096 A | 9/2000 | Hassard |
| RE36,905 E | 10/2000 | Noble et al. |
| 6,125,792 A | 10/2000 | Gee |
| 6,129,638 A | 10/2000 | Davis |
| 6,129,691 A | 10/2000 | Ruppert |
| 6,156,001 A | 12/2000 | Frangi et al. |
| 6,159,248 A | 12/2000 | Gramnas |
| 6,182,288 B1 | 2/2001 | Kibbee |
| 6,190,343 B1 | 2/2001 | Heinz et al. |
| D438,624 S | 3/2001 | Reina |
| 6,206,932 B1 | 3/2001 | Johnson |
| 6,213,968 B1 | 4/2001 | Heinz et al. |
| 6,227,937 B1 | 5/2001 | Principe |
| 6,245,033 B1 | 6/2001 | Martin |
| 6,254,561 B1 | 7/2001 | Borden |
| 6,256,798 B1 | 7/2001 | Egolf et al. |
| 6,267,390 B1 | 7/2001 | Maravetz et al. |
| 6,282,729 B1 | 9/2001 | Oikawa et al. |
| 6,289,558 B1 | 9/2001 | Hammerslag |
| 6,315,746 B1 | 11/2001 | Garth et al. |
| 6,322,529 B1 | 11/2001 | Chung |
| 6,325,023 B1 | 12/2001 | Elnatan |
| 6,338,723 B1 | 1/2002 | Carpenter et al. |
| 6,401,786 B1 | 6/2002 | Tedeschi et al. |
| 6,413,232 B1 | 7/2002 | Townsend et al. |

(56) References Cited

U.S. PATENT DOCUMENTS

| | | |
|---|---|---|
| 6,416,074 B1 | 7/2002 | Maravetz et al. |
| 6,419,652 B1 | 7/2002 | Slautterback |
| 6,425,876 B1 | 7/2002 | Frangi et al. |
| 6,428,493 B1 | 8/2002 | Pior et al. |
| 6,432,073 B2 | 8/2002 | Pior et al. |
| 6,471,665 B1 | 10/2002 | Milbourn et al. |
| 6,478,759 B1 | 11/2002 | Modglin et al. |
| 6,502,577 B1 | 1/2003 | Bonutti |
| 6,503,213 B2 | 1/2003 | Bonutti |
| 6,517,502 B2 | 2/2003 | Heyman et al. |
| 6,540,703 B1 | 4/2003 | Lerman |
| 6,589,195 B1 | 7/2003 | Schwenn et al. |
| 6,602,214 B2 | 8/2003 | Heinz et al. |
| 6,605,052 B1 | 8/2003 | Cool et al. |
| 6,609,642 B2 | 8/2003 | Heinz et al. |
| 6,623,419 B1 | 9/2003 | Smith et al. |
| 6,652,596 B2 | 11/2003 | Smith et al. |
| 6,676,617 B1 | 1/2004 | Miller |
| 6,676,620 B2 | 1/2004 | Schwenn et al. |
| 6,688,943 B2 | 2/2004 | Nagaoka |
| 6,689,080 B2 | 2/2004 | Castillo |
| 6,702,770 B2 | 3/2004 | Bremer et al. |
| 6,711,787 B2 | 3/2004 | Jungkind et al. |
| 6,726,643 B1 | 4/2004 | Martin |
| 6,769,155 B2 | 8/2004 | Hess et al. |
| 6,770,047 B2 | 8/2004 | Bonutti |
| 6,790,191 B1 | 9/2004 | Hendricks |
| 6,802,442 B1 | 10/2004 | Thompson |
| D499,806 S | 12/2004 | Machin et al. |
| 6,827,653 B2 | 12/2004 | Be |
| D501,078 S | 1/2005 | Cabana |
| 6,893,098 B2 | 5/2005 | Kohani |
| 6,893,411 B1 * | 5/2005 | Modglin ................. 602/23 |
| 6,913,585 B2 | 7/2005 | Salmon et al. |
| 6,921,375 B2 | 7/2005 | Kihara |
| 6,921,377 B2 | 7/2005 | Bonutti |
| 6,923,780 B2 | 8/2005 | Price et al. |
| 6,926,685 B1 | 8/2005 | Modglin |
| 6,936,021 B1 | 8/2005 | Smith |
| 6,942,630 B2 | 9/2005 | Behan |
| 6,951,547 B1 | 10/2005 | Park et al. |
| 6,962,572 B1 | 11/2005 | Zahiri |
| 6,964,644 B1 | 11/2005 | Garth |
| 6,991,611 B2 | 1/2006 | Rhee |
| 7,001,348 B2 | 2/2006 | Garth et al. |
| 7,001,350 B2 | 2/2006 | Grosso |
| 7,025,737 B2 | 4/2006 | Modglin |
| 7,028,873 B1 | 4/2006 | Collier et al. |
| 7,034,251 B1 | 4/2006 | Child et al. |
| 7,048,707 B2 | 5/2006 | Schwenn et al. |
| 7,074,204 B2 | 7/2006 | Fujii et al. |
| 7,083,584 B2 | 8/2006 | Coligado |
| 7,083,585 B2 | 8/2006 | Latham |
| 7,087,032 B1 | 8/2006 | Ikeda |
| 7,101,348 B2 | 9/2006 | Garth et al. |
| 7,118,543 B2 | 10/2006 | Telles et al. |
| 7,128,724 B2 | 10/2006 | Marsh |
| 7,134,224 B2 | 11/2006 | Elkington et al. |
| 7,137,973 B2 | 11/2006 | Plauche et al. |
| 7,140,691 B2 | 11/2006 | Kohani |
| 7,166,083 B2 | 1/2007 | Bledsoe |
| 7,186,229 B2 | 3/2007 | Schwenn et al. |
| 7,198,610 B2 | 4/2007 | Ingimundarson et al. |
| 7,201,727 B2 | 4/2007 | Schwenn et al. |
| 7,235,059 B2 | 6/2007 | Mason et al. |
| 7,281,341 B2 | 10/2007 | Reagan et al. |
| 7,306,571 B2 | 12/2007 | Schwenn et al. |
| 7,306,573 B2 | 12/2007 | Bonutti |
| 7,309,304 B2 | 12/2007 | Stewart et al. |
| 7,316,660 B1 | 1/2008 | Modglin |
| 7,320,670 B1 | 1/2008 | Modglin |
| 7,322,950 B2 | 1/2008 | Modglin |
| 7,329,231 B2 | 2/2008 | Frank |
| 7,331,126 B2 | 2/2008 | Johnson |
| 7,351,368 B2 | 4/2008 | Abrams |
| 7,402,147 B1 | 7/2008 | Allen |
| 7,404,804 B2 | 7/2008 | Bonutti |
| 7,416,565 B1 | 8/2008 | Al-Turaikl |
| 7,438,698 B2 | 10/2008 | Daiju |
| 7,473,235 B2 | 1/2009 | Schwenn et al. |
| 7,476,185 B2 | 1/2009 | Drennan |
| 7,513,018 B2 | 4/2009 | Koenig et al. |
| 7,549,970 B2 | 6/2009 | Tweardy |
| 7,578,798 B2 | 8/2009 | Rhee |
| 7,591,050 B2 | 9/2009 | Hammerslag |
| 7,597,671 B2 | 10/2009 | Baumgartner et al. |
| 7,597,672 B2 | 10/2009 | Kruijsen et al. |
| 7,600,660 B2 | 10/2009 | Kasper et al. |
| 7,615,021 B2 | 11/2009 | Nordt, III et al. |
| 7,618,386 B2 | 11/2009 | Nordt, III et al. |
| 7,618,389 B2 | 11/2009 | Nordt, III et al. |
| 7,654,972 B2 | 2/2010 | Alleyne |
| 7,662,121 B2 | 2/2010 | Zours |
| 7,670,306 B2 | 3/2010 | Nordt, III et al. |
| 7,682,219 B2 | 3/2010 | Falla |
| 7,699,797 B2 | 4/2010 | Nordt, III et al. |
| 7,704,219 B2 | 4/2010 | Nordt, III et al. |
| 7,727,048 B2 | 6/2010 | Gransberry |
| 7,727,174 B2 | 6/2010 | Chang et al. |
| 7,775,999 B2 | 8/2010 | Brown |
| 7,806,842 B2 | 10/2010 | Stevenson et al. |
| 7,815,585 B2 | 10/2010 | Vollbrecht |
| 7,819,831 B2 | 10/2010 | Dellanno |
| 7,833,182 B2 | 11/2010 | Hughes |
| 7,842,000 B2 | 11/2010 | Lai et al. |
| 7,857,776 B2 | 12/2010 | Frisbie |
| 7,862,529 B2 | 1/2011 | Brown |
| 7,862,621 B2 | 1/2011 | Kloos et al. |
| 7,871,388 B2 | 1/2011 | Brown |
| 7,878,998 B2 | 2/2011 | Nordt, III et al. |
| 7,887,500 B2 | 2/2011 | Nordt, III et al. |
| 7,914,473 B2 | 3/2011 | Josey |
| D636,494 S | 4/2011 | Garth et al. |
| 7,922,680 B2 | 4/2011 | Nordt, III et al. |
| 7,950,112 B2 | 5/2011 | Hammerslag et al. |
| 7,954,204 B2 | 6/2011 | Hammerslag et al. |
| 7,959,591 B2 | 6/2011 | Powers et al. |
| 7,993,296 B2 | 8/2011 | Nordt, III et al. |
| 8,002,724 B2 | 8/2011 | Hu et al. |
| 8,006,877 B2 | 8/2011 | Lowry et al. |
| 8,038,635 B2 | 10/2011 | Dellanno |
| 8,038,637 B2 | 10/2011 | Bonutti |
| 8,047,893 B2 | 11/2011 | Fenske |
| 8,048,014 B2 | 11/2011 | Brown |
| 8,066,161 B2 | 11/2011 | Green et al. |
| 8,066,654 B2 | 11/2011 | Sandifer et al. |
| 8,091,182 B2 | 1/2012 | Hammerslag et al. |
| 8,142,377 B2 | 3/2012 | Garth et al. |
| 8,162,194 B2 | 4/2012 | Gleason |
| 8,162,864 B2 | 4/2012 | Kruijsen et al. |
| 8,172,779 B2 | 5/2012 | Ingimundarson et al. |
| 8,214,926 B2 | 7/2012 | Brown |
| 8,216,167 B2 | 7/2012 | Garth et al. |
| 8,303,528 B2 | 11/2012 | Ingimundarson et al. |
| 8,308,669 B2 * | 11/2012 | Nace ........................ 602/16 |
| 8,308,670 B2 | 11/2012 | Sandifer et al. |
| 8,308,869 B2 | 11/2012 | Gardner et al. |
| 8,372,023 B2 | 2/2013 | Garth et al. |
| 8,556,840 B2 | 10/2013 | Burke et al. |
| 8,597,222 B2 | 12/2013 | Lucero et al. |
| 8,795,215 B2 | 8/2014 | Rossi |
| 8,956,315 B2 | 2/2015 | Garth et al. |
| 2001/0020144 A1 | 9/2001 | Heinz et al. |
| 2001/0031936 A1 | 10/2001 | Pior et al. |
| 2002/0032397 A1 | 3/2002 | Coligado |
| 2002/0068890 A1 | 6/2002 | Schwenn et al. |
| 2002/0148461 A1 | 10/2002 | Heinz et al. |
| 2002/0158097 A1 | 10/2002 | Beale |
| 2003/0000986 A1 | 1/2003 | Smith |
| 2003/0028952 A1 | 2/2003 | Fujii et al. |
| 2003/0125650 A1 | 7/2003 | Grosso |
| 2003/0125705 A1 | 7/2003 | Ruman et al. |
| 2003/0220594 A1 | 11/2003 | Halvorson et al. |
| 2003/0229301 A1 | 12/2003 | Coligado |

(56) References Cited

U.S. PATENT DOCUMENTS

| | | |
|---|---|---|
| 2004/0024340 A1 | 2/2004 | Schwenn et al. |
| 2004/0050391 A1 | 3/2004 | Kiwala et al. |
| 2004/0082895 A1 | 4/2004 | Price et al. |
| 2004/0097857 A1 | 5/2004 | Reinecke et al. |
| 2004/0108350 A1 | 6/2004 | Warren |
| 2004/0116260 A1 | 6/2004 | Drennan |
| 2004/0132380 A1 | 7/2004 | Kihara |
| 2004/0133138 A1 | 7/2004 | Modglin |
| 2004/0143204 A1 | 7/2004 | Salmon et al. |
| 2005/0054960 A1 | 3/2005 | Telles et al. |
| 2005/0059917 A1 | 3/2005 | Garth et al. |
| 2005/0067816 A1 | 3/2005 | Buckman |
| 2005/0081339 A1 | 4/2005 | Sakabayashi |
| 2005/0131323 A1 | 6/2005 | Bledsoe |
| 2005/0137508 A1 | 6/2005 | Miller |
| 2005/0154337 A1 | 7/2005 | Meyer |
| 2005/0160627 A1 | 7/2005 | Dalgaard et al. |
| 2005/0165338 A1 | 7/2005 | Iglesias et al. |
| 2005/0228325 A1 | 10/2005 | Zours et al. |
| 2005/0240134 A1 | 10/2005 | Brown |
| 2005/0251074 A1 | 11/2005 | Latham |
| 2005/0267390 A1 | 12/2005 | Garth et al. |
| 2005/0273025 A1 | 12/2005 | Houser |
| 2006/0011690 A1 | 1/2006 | Bareno |
| 2006/0052733 A1 | 3/2006 | Schwenn et al. |
| 2006/0064048 A1 | 3/2006 | Stano |
| 2006/0079821 A1 | 4/2006 | Rauch |
| 2006/0129077 A1 | 6/2006 | Parizot |
| 2006/0135900 A1 | 6/2006 | Ingimundarson et al. |
| 2006/0135901 A1* | 6/2006 | Ingimundarson et al. ..... 602/26 |
| 2006/0155229 A1 | 7/2006 | Ceriani et al. |
| 2006/0156517 A1 | 7/2006 | Hammerslag et al. |
| 2006/0206992 A1 | 9/2006 | Godshaw et al. |
| 2007/0152007 A1 | 7/2007 | Kauss et al. |
| 2007/0167895 A1* | 7/2007 | Gramza et al. ................. 602/26 |
| 2007/0179417 A1 | 8/2007 | Schwenn et al. |
| 2007/0185425 A1 | 8/2007 | Einarsson et al. |
| 2008/0091132 A1 | 4/2008 | Bonutti |
| 2008/0195010 A1 | 8/2008 | Lai et al. |
| 2008/0208091 A1 | 8/2008 | Vollbrecht et al. |
| 2008/0249448 A1* | 10/2008 | Stevenson et al. ............. 602/16 |
| 2008/0262401 A1 | 10/2008 | Wagner et al. |
| 2008/0302839 A1 | 12/2008 | Murdoch et al. |
| 2008/0319362 A1 | 12/2008 | Joseph |
| 2009/0025115 A1 | 1/2009 | Duffy et al. |
| 2009/0030353 A1 | 1/2009 | Bonutti et al. |
| 2009/0030359 A1 | 1/2009 | Wikenheiser et al. |
| 2009/0062704 A1 | 3/2009 | Brown et al. |
| 2009/0082707 A1 | 3/2009 | Rumsey |
| 2009/0100649 A1 | 4/2009 | Bar et al. |
| 2009/0124948 A1 | 5/2009 | Ingimundarson et al. |
| 2009/0127308 A1 | 5/2009 | Mori et al. |
| 2009/0182253 A1* | 7/2009 | Grim et al. ..................... 602/16 |
| 2009/0192425 A1 | 7/2009 | Garth et al. |
| 2009/0198166 A1 | 8/2009 | Shlomovitz |
| 2009/0275871 A1 | 11/2009 | Liu |
| 2009/0287128 A1 | 11/2009 | Ingimundarson et al. |
| 2010/0010568 A1 | 1/2010 | Brown |
| 2010/0037369 A1 | 2/2010 | Reichert |
| 2010/0139057 A1 | 6/2010 | Soderberg et al. |
| 2010/0204630 A1 | 8/2010 | Sandifer et al. |
| 2010/0217167 A1 | 8/2010 | Ingimundarson et al. |
| 2010/0256717 A1 | 10/2010 | Brown |
| 2010/0268139 A1 | 10/2010 | Garth |
| 2010/0268141 A1 | 10/2010 | Bannister |
| 2010/0274364 A1 | 10/2010 | Pacanowsky et al. |
| 2010/0299959 A1 | 12/2010 | Hammerslag et al. |
| 2010/0318010 A1 | 12/2010 | Sandifer et al. |
| 2011/0000005 A1 | 1/2011 | Brown |
| 2011/0009793 A1 | 1/2011 | Lucero et al. |
| 2011/0046528 A1 | 2/2011 | Stevenson et al. |
| 2011/0082402 A1 | 4/2011 | Oddou et al. |
| 2011/0098618 A1 | 4/2011 | Fleming |
| 2011/0105971 A1 | 5/2011 | Ingimundarson et al. |
| 2011/0137221 A1 | 6/2011 | Brown |
| 2011/0144551 A1 | 6/2011 | Johnson |
| 2011/0152737 A1 | 6/2011 | Burke et al. |
| 2011/0178448 A1 | 7/2011 | Einarsson |
| 2011/0184326 A1 | 7/2011 | Ingimundarson et al. |
| 2011/0266384 A1 | 11/2011 | Goodman et al. |
| 2012/0010547 A1 | 1/2012 | Hinds |
| 2012/0022420 A1 | 1/2012 | Sandifer et al. |
| 2012/0029404 A1 | 2/2012 | Weaver, II et al. |
| 2012/0197167 A1 | 8/2012 | Kruijsen et al. |
| 2012/0204381 A1 | 8/2012 | Ingimundarson et al. |
| 2012/0232450 A1 | 9/2012 | Garth et al. |
| 2012/0323154 A1 | 12/2012 | Ingimundarson et al. |
| 2013/0006158 A1 | 1/2013 | Ingimundarson et al. |
| 2013/0007946 A1 | 1/2013 | Brown |
| 2013/0012853 A1 | 1/2013 | Brown |
| 2013/0158457 A1 | 6/2013 | Garth et al. |
| 2013/0184628 A1 | 7/2013 | Ingimundarson et al. |
| 2013/0190670 A1 | 7/2013 | Von Zieglauer |
| 2013/0211302 A1 | 8/2013 | Brown |
| 2013/0237891 A1 | 9/2013 | Fryman et al. |
| 2013/0281901 A1 | 10/2013 | Ochoa |
| 2013/0298914 A1 | 11/2013 | Shibaya et al. |
| 2014/0200121 A1 | 7/2014 | Von Hoffmann et al. |
| 2014/0336020 A1 | 11/2014 | Von Hoffmann et al. |

FOREIGN PATENT DOCUMENTS

| | | |
|---|---|---|
| AU | 2010286851 A1 | 3/2012 |
| AU | 2010286851 A2 | 5/2012 |
| CA | 2112789 A1 | 1/1994 |
| CA | 2114387 A1 | 1/1994 |
| CA | 2767353 A1 | 1/2011 |
| CA | 2772296 A1 | 3/2011 |
| CH | 577 282 A5 | 11/1974 |
| CH | 612 076 A5 | 1/1977 |
| CH | 624 001 A5 | 12/1977 |
| CN | 1311648 A | 9/2001 |
| CN | 201101603 Y | 8/2008 |
| CN | 102470040 A | 5/2012 |
| DE | 1197192 B | 7/1965 |
| DE | 38 22 113 A1 | 6/1988 |
| DE | 8804683 U1 | 6/1988 |
| DE | 88 04 683.4 | 7/1988 |
| DE | 93 15 776.2 U1 | 10/1993 |
| DE | 295 03 552.8 U1 | 3/1995 |
| DE | 199 45 045 A1 | 9/1999 |
| DE | 20204747 U1 | 7/2002 |
| DE | 103 29 454 A1 | 1/2005 |
| DE | 202004015328 U1 | 2/2005 |
| DE | 202005007124 U1 | 6/2005 |
| DE | 20 2009 004 817 U1 | 9/2010 |
| EP | 393 380 B1 | 3/1990 |
| EP | 589 232 B1 | 8/1993 |
| EP | 589 233 B1 | 8/1993 |
| EP | 651 954 B1 | 11/1993 |
| EP | 614 624 A1 | 12/1993 |
| EP | 614 625 A1 | 1/1994 |
| EP | 657 149 A1 | 6/1995 |
| EP | 0657149 A1 | 6/1995 |
| EP | 693 260 B1 | 7/1995 |
| EP | 1 159 940 A2 | 12/2001 |
| EP | 1159940 A2 | 12/2001 |
| EP | 1 236 412 A1 | 2/2002 |
| EP | 1 342 423 A1 | 9/2003 |
| EP | 1 588 678 A1 | 10/2005 |
| EP | 1 743 608 A2 | 1/2007 |
| EP | 1 985 264 A1 | 10/2008 |
| EP | 2 200 545 A1 | 6/2010 |
| EP | 2451412 A1 | 5/2012 |
| EP | 2473072 A1 | 7/2012 |
| FR | 1104562 A | 11/1955 |
| FR | 2 757 073 A1 | 6/1998 |
| FR | 2 952 807 A1 | 5/2011 |
| FR | 2952807 A1 | 5/2011 |
| GB | 826 041 A | 12/1959 |
| GB | 909970 A | 11/1962 |
| GB | 2 133 289 A | 7/1984 |
| JP | H09-273582 A | 10/1997 |
| JP | 3031760 U | 9/1998 |

(56) References Cited

FOREIGN PATENT DOCUMENTS

| JP | H10-237708 A | 9/1998 |
|---|---|---|
| JP | 2000-290331 A | 10/2000 |
| JP | 2001-204851 A | 7/2001 |
| JP | 2003-175063 A | 6/2003 |
| JP | 2004-016732 | 1/2004 |
| JP | 2004-041666 | 2/2004 |
| JP | 2004209050 A | 7/2004 |
| JP | 2007-291536 A | 11/2007 |
| JP | 3142546 U | 6/2008 |
| JP | 2009-082697 A | 4/2009 |
| JP | 2012-011550 A | 1/2012 |
| JP | 2013503268 A | 1/2013 |
| JP | 2013-536010 A | 9/2013 |
| WO | 9401496 A | 1/1994 |
| WO | 95/03720 A2 | 2/1995 |
| WO | 97/03581 A1 | 2/1997 |
| WO | 00/53045 A1 | 9/2000 |
| WO | 2004/110197 A2 | 12/2004 |
| WO | 2005086752 A2 | 9/2005 |
| WO | 2005086752 A3 | 9/2005 |
| WO | 2006/121413 A1 | 11/2006 |
| WO | 2009/017499 A1 | 2/2009 |
| WO | 2009/017949 A1 | 2/2009 |
| WO | 2009/052031 A1 | 4/2009 |
| WO | 2009068503 A1 | 6/2009 |
| WO | 2011005430 A1 | 1/2011 |
| WO | 2011025675 A1 | 3/2011 |
| WO | 2011/066323 A1 | 6/2011 |
| WO | 2012/029917 A1 | 3/2012 |
| WO | 2013016670 A1 | 1/2013 |

OTHER PUBLICATIONS

Supplemental EP Search Report from EP Application No. 98920943, Dec. 7, 2004.
International Search Report from PCT Application No. PCT/US2010/000601, Jun. 28, 2010.
International Preliminary Report on Patentability from PCT Application No. PCT/US2010/000601, Aug. 30, 2011.
International Search Report from PCT Application No. PCT/US2012/024619, May 16, 2012.
Sato, Ena et al., Effect of the WISH-type hip brace on functional mobility in patients with osteoarthritis of the hip: evaluation using the Timed Up & Go Test, Prosthetics and Orthotics International 2012 36:25 originally published online Nov. 17, 2011, http://poi.sagepub.com/content/36/1/25 [retrieved from Internet on Jan. 22, 2014].
Silosheath Brochure, Soft Socket Gel Liner, 4 pages, 1994.
International Search Report from PCT Application No. PCT/US98/08975, Jul. 8, 1998.
International Search Report from International PCT Application No. PCT/JP2011/069929, dated Oct. 18, 2011.
International Search Report from corresponding International PCT Application No. PCT/US2014/012860, Apr. 17, 2014.
Pamphlet—"Bledsoe Phillippon K.A.F. Positioning Kit, Application Instructions (CP020205 Rev B 04/07), New Hip Arthroscopy Padding and Positioning Kit", Council Directive 93/42/EEC of Jun. 14, 1993 concerning Medical Devices, 2 pages.
Mehlman, Charles T. et al., "Hyphenated History: Knight-Taylor Spinal Orthosis"; American Journal of Orthopedics; Jun. 2000; pp. 479-483, vol. 29, Issue 6.
Pamphlet—"Bledsoe Phillippon K.A.F. Positioning Kit", Bledsoe Brace Systems, Medical Technology Inc., 2004, 2 pages.
Posture Control Brace. Soft Form, Orthopaedic by Design, FLA Orthopedics, Inc., 1 page; 2004. http://www.flaorthopedics.com.
Michael Pfiefer, MD et al., "Effects of a New Spinal Orthosis on Posture, Trunk Strength, and Quality of Life in Women with Postmenopausal Osteoporosis—a Randomized Trial", American Journal of Physical Medicine & Rehabilitation, vol. 83, No. 3, Mar. 2004, USA, pp. 177-186.
Scoliosis Specialists. About the SpineCor Brace; 2006-2012; http://www.scoliosisspecialists.com/aboutspinecorbrace.html. Retrieved from Internet on Aug. 1, 2013.
Hsu et al., "Principles and Components of Spinal Orthoses", AAOS Atlas of Orthoses and Assistive Devices, 4th Ed., Chapter 7, 2008, pp. 89-111.
International Search Report and Written Opinion from corresponding International PCT Application No. PCT/US2010/002893, Feb. 22, 2011.
International Search Report from corresponding International PCT Application No. PCT/US2013/021170, Apr. 12, 2013.
Spinomed Brochure—Spinal Orthosis for Vertebral Extension in Osteoporosis; Stellar Orthotics and Prosthetics Group, 2 pages, retrieved from Internet Sep. 23, 2013. http://www.stellaroandp.com/spotlight.html.
International Search Report from corresponding International PCT Application No. PCT/US2013/066425, Mar. 18, 2014.
Examination report from EP Application No. 12740242.8, Sep. 3, 2015.

* cited by examiner

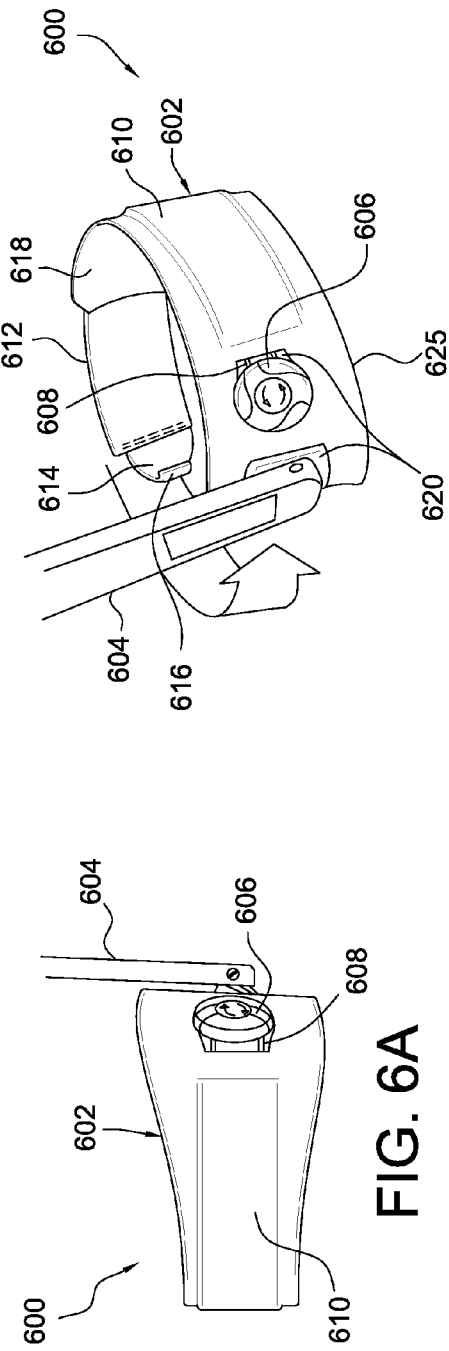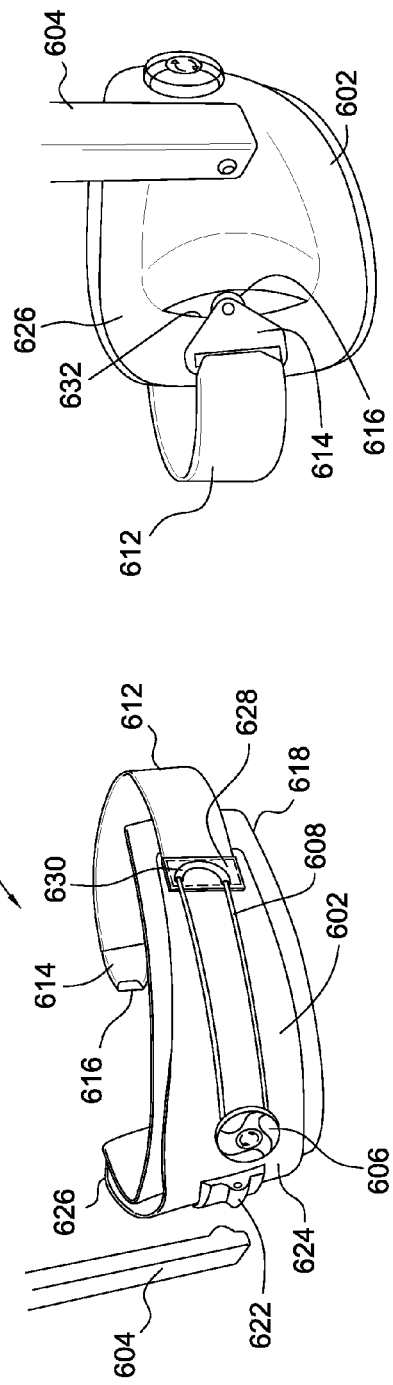

ORTHOPEDIC DEVICE, USE OF ORTHOPEDIC DEVICE AND METHOD FOR PRODUCING SAME

CROSS-REFERENCE TO RELATED APPLICATIONS

This application claims the benefit of priority from U.S. provisional application Ser. No. 61/498,831, filed on Jun. 20, 2011. The entirety of the contents of this priority application is incorporated herein.

This application incorporates by reference the entirety of the following documents: U.S. patent application Ser. No. 12/353,555, filed on Jan. 14, 2009 and published as U.S. patent application publication No. 2009/0124948 A1, U.S. Pat. No. 8,172,779, granted on May 8, 2012, U.S. Pat. No. 7,597,672, granted on Oct. 6, 2009, and U.S. Pat. No. 7,198,610, granted on Apr. 3, 2007.

FIELD OF ART

The embodiments of this disclosure are directed to orthopedic devices, particularly to a hip orthosis for treating the hip and the use thereof, and to methods used to produce the orthopedic device.

BACKGROUND

Hip orthoses may be used for preventing hip dislocation, and provide early mobilization after hip surgery while minimizing post-surgical complications. Certain surgical operations include hip joint replacements or complete or partial revision surgery, and hip arthroscopy. These orthoses can be used to reduce the length of hospitalization and rehabilitation, and the total period for convalescence. Hip orthoses may also be used to treat persistent hip pain and non-operable hip deformities.

Prophylaxis or hip dislocation is a problem that occurs when the femoral head is displaced in the acetabulum or the hip socket. Typically, after hip surgery, a hip orthosis is needed for immobilization and support to aid in rehabilitation by preventing such a dislocation again.

The head of the femur meets the pelvis as the acetabulum and forms the hip joint. The head of the femur ("femoral head") and the acetabulum form as a ball-and-socket joint that allows for flexion, extension, abduction, adduction and circumduction. The hip is arranged for weight bearing, and there are connective ligaments for supporting the hip joint.

Known hip orthoses used to prevent hip dislocation typically may have an adjustable hinge which only allows for rotation of the upper leg about the hip joint in forward and backward directions. These hip orthoses have the drawback of failing to provide a dynamic abducting force on the leg throughout an entire range of motion. In other words, the abducting force may be provided while standing, but is not applied when sitting. Because the conventional orthoses hold the leg in abduction rigidly, this may lead to abnormal gait patterns and compliance issues.

SUMMARY

The hip orthosis according to this disclosure is a directed to an orthopedic device in the form of a hip orthosis that may be used to protect primary arthroplasty patients at risk of dislocation, hip revision, recurrent dislocations, inoperable hip abnormalities or for preventative use in everyday living. Certain embodiments may also be used to treat osteoarthritis of the hip.

Embodiments of the hip orthosis described herein secure and control the femoral head in the acetabulum by providing a dynamic force on the leg and hip socket to prevent dislocation and treat instances of osteoarthritis. This dynamic force mechanism follows the anatomical motion of the hip joint by maintaining the prescribed flexion and extension restrictions. Moreover, features of the hip orthosis attribute to a more stable and versatile orthosis over conventional braces.

The hip orthosis allows for dynamic abduction due to a hinge-free design. The hip orthosis includes a spring steel rod arranged to exert a dynamic abduction force to the leg throughout the range of motion of the user, even while sitting. A sliding joint is included which follows the anatomical motion of the hip joint while maintaining flexion and extension restrictions.

The hip orthosis has a low profile configuration which offers improved comfort, cosmesis and patient compliance. The hip orthosis is preferably modular in that it provides optimal user fit and a reduction in inventory stock levels.

In an embodiment of the disclosure, an orthopedic device such as a hip orthosis, may include an elongate and rigid or semi-rigid strut assembly, an arcuate cuff pivotally secured to the strut assembly, and a strap securing to the cuff and forming an adjustable circumferential configuration therewith.

The device may include a rotational mechanism for locking the location of the cuff relative to the strut assembly. One of the cuff or the rotational mechanism may include a plurality of spaced protrusions arranged to place the cuff at a plurality of preselected angles relative to the strut assembly. The device may have a mounting clip attached to the cuff coupling to the strut assembly and permitting rotation of the cuff relative to the strut assembly.

The cuff may be flexible and is preferably rotatable to right or left leg configurations relative to the strut assembly.

The device can have a tensioning device mounted on the cuff and coupled to the strap. The tensioning device is preferably arranged for incrementally adjusting the circumference of a circumferential configuration formed by the strap and the cuff. A first end of the strap secures to the tensioning device and a second end of the strap couples to the cuff. The strap may include a mounting bracket securable to an opening formed by the cuff.

A method according to the disclosure is provided for using the tensioning device to adjust a circumferential configuration in an orthopedic device. Alternatively, the tensioning device and cuff and strap arrangement may be used in a variety of different orthopedic devices and not exclusively for hip orthoses.

The device may additional include a soft-good assembly connected to the strut assembly. The soft-good assembly may have a flexible stay embedded within with a plurality of layers. The soft-good assembly is adapted to form an adjustable circumferential loop with the stay only located within a segment short of the circumference of the loop. The soft-good assembly may define a pocket and a plate can be located adjacent to or spaced away from the pocket. The plate can depend from the strut assembly. The plate may be mounted at a first end of the strut assembly, and the cuff is mounted on a second end of the strut assembly.

A method according to the disclosure is provided for forming the soft-good assembly inclusive of the flexible stay and a plurality of textile layers surrounding the stay.

The numerous advantages, features and functions of the various embodiments herein will become readily apparent and better understood in view of the following description and accompanying drawings. The following description is not intended to limit the scope of the hip orthosis, but instead merely provides exemplary embodiments for ease of understanding.

BRIEF DESCRIPTION OF THE DRAWINGS

These and other features, aspects, and advantages of the present invention will become better understood with regard to the following description, appended claims, and accompanying drawings where:

FIGS. 6A-6D are perspective views showing a variation of the thigh cuff assembly according to the hip orthosis of FIGS. 4A-4C.

Figure 1A:
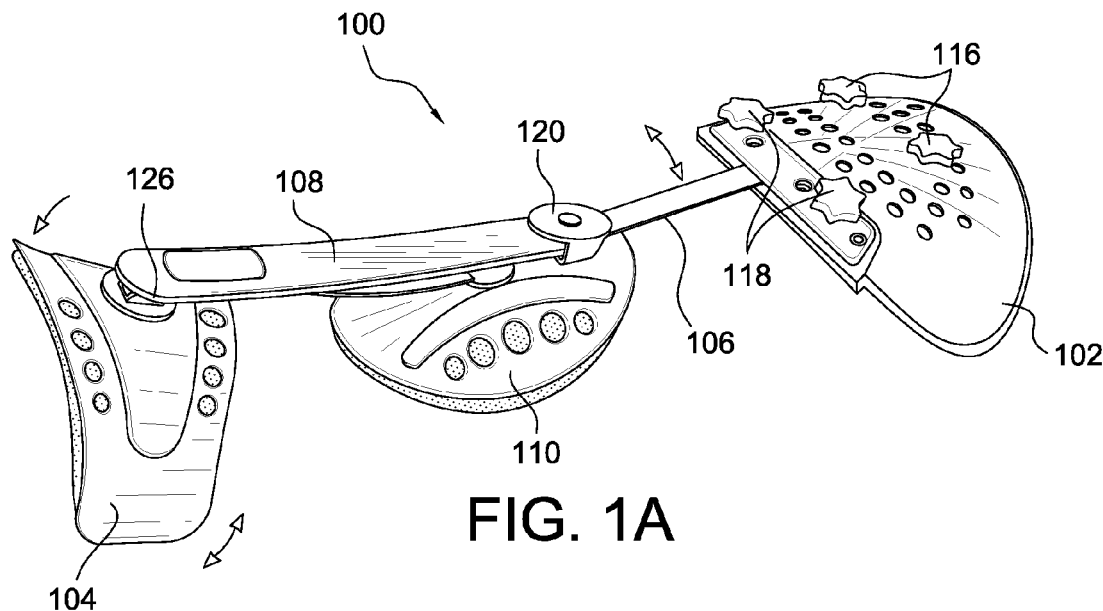
FIG. 1A is a perspective view showing an embodiment of a hip orthosis frame.

In the various figures, similar elements are provided with similar reference numbers. It should be noted that the drawing figures are not necessarily drawn to scale, or proportion, but instead are drawn to provide a better understanding of the components thereof, and are not intended to be limiting in scope, but rather provide exemplary illustrations.

DETAILED DESCRIPTION OF VARIOUS EMBODIMENTS

Figure 1B:
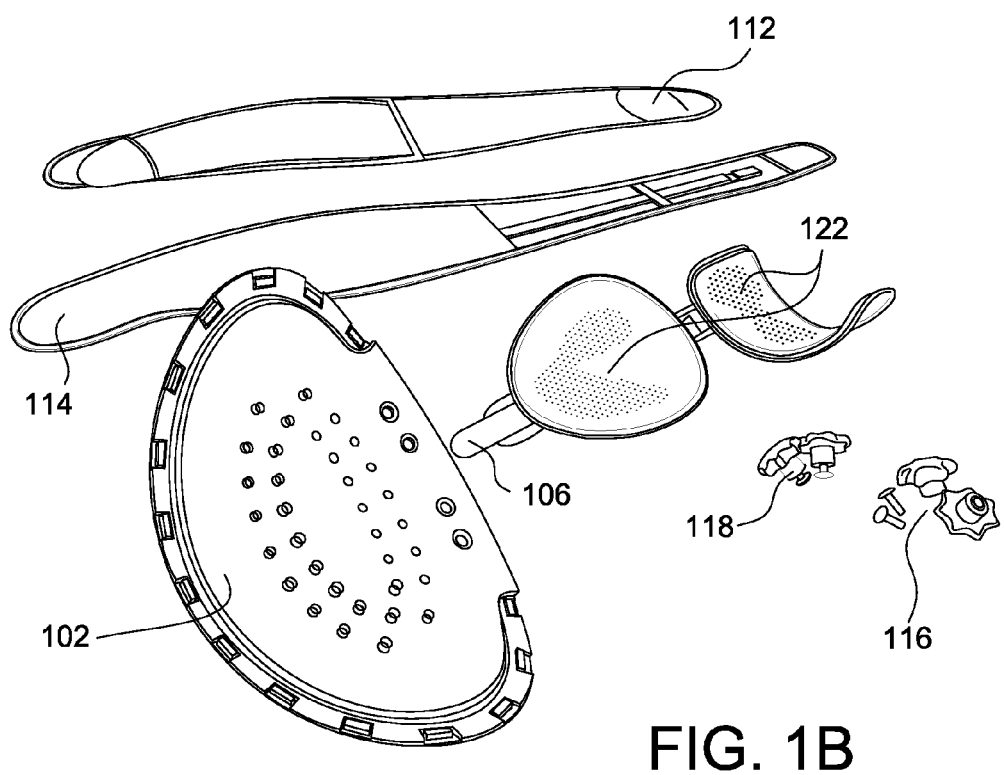
FIG. 1B is a perspective view showing the hip orthosis frame of FIG. 1A and a soft-good assembly for use with the hip orthosis frame.
Figure 1C:
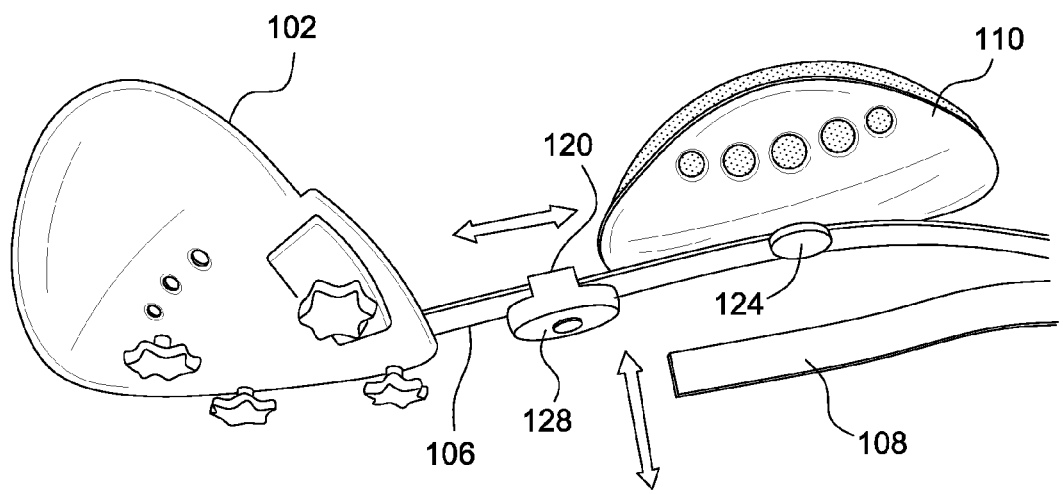
FIG. 1C is a schematic view showing adjustment of the hip orthosis of FIG. 1A.

FIGS. 1A-1C illustrate an embodiment of the hip orthosis, which incorporates some of the basic functions of the hip orthosis taught in part in U.S. Pat. No. 7,597,672. According to this embodiment, a hip orthosis 100 includes a hip plate 102 adapted to secure to the hip of the user and remain in place with a pelvic strap assembly 112. The orthosis includes a lower thigh cuff 104 adapted to secure to the thigh of the user and remain in place with a thigh strap 114

A spring rod 106 connects the hip plate 102 and the lower thigh cuff 104 to one another. A lower spring rod support 108 and an upper spring rod support 120 engage the spring rod 106. An upper thigh pad or shell 110 slidably engages the spring rod 106.

The spring rod 106 is pivotally connected to the lower thigh cuff 104. As for the hip plate 102, the spring rod 106 has an end portion inserted within the hip plate 102, and slides side to side relative to the hip plate 102 with the motion restricted by restriction stops 118, and flexion and extension stops 116 limit movements of the hip plate 102 and spring rod 106 relative to one another. The flexion and extensions stops 116 and the restriction stops 118 are adjustable on the hip plate 102.

The stops are preassembled for the right hip and range of motion of 0° extension to 70° flexion. If the hip orthosis is fitted for the left hip and the range of motion restriction is adjusted, the restriction stops and the flexion/extension stops can be placed in the correct location. Two restriction stops, one flexion stop and one extension stop, are arranged to restrict the range of motion. Guides may be provided on the inside and outside portions of the hip plate for reference, however the resultant flexion and extension angle should be verified to assure that the correct is angle is set.

If the desired angle is between 0° and 70°, the restriction stops are placed in two inner openings (closest to the spring rod). If the desired angle is between 60° and 90°, the restriction stops are placed in two outer openings (farthest from the spring rod). The flexion/extension stops are placed according to indicia on the inside and/or the outside of the hip plate.

As depicted in FIG. 1C, the upper thigh pad 110 is adjusted up and down by sliding along the spring rod 106 by loosening the upper spring rod support screw 128 and maintaining the upper and lower spring rod supports 120, 108 together. The lower spring rod support 108 can be pivotally drawn away from spring rod 106 at the pivot point 126. The locking screw 124 maintaining the upper thigh cuff 110 can be loosened so as to permit movement thereof.

The hip plate 102 is placed into an opening of the pelvic strap assembly 112. The pelvic strap assembly 112 has a side formed from stretchable material which should face outwardly so it can conform to the flexion and extension stops 116, and restriction stops 118. When positioning the hip orthosis on the user, the pelvic strap assembly 112 may include indicia arranged to be align directly superior to the greater trochanter of the user's femur. The indicia is then aligned with the top of the strap with the tip of the iliac crest.

The pelvic strap assembly 112 includes a finger pocket at one end thereof in which the user places fingers or a hand. The strap is then wrapped around the pelvis. The pelvic strap assembly 112 includes an inner strap having first and second ends with the first end portion which is secured to an opposed second end portion of the pelvic wrap. An outer strap generally overlapping the inner strap is then secured to a surface over at least one of the first and second end portions.

Figure 2:
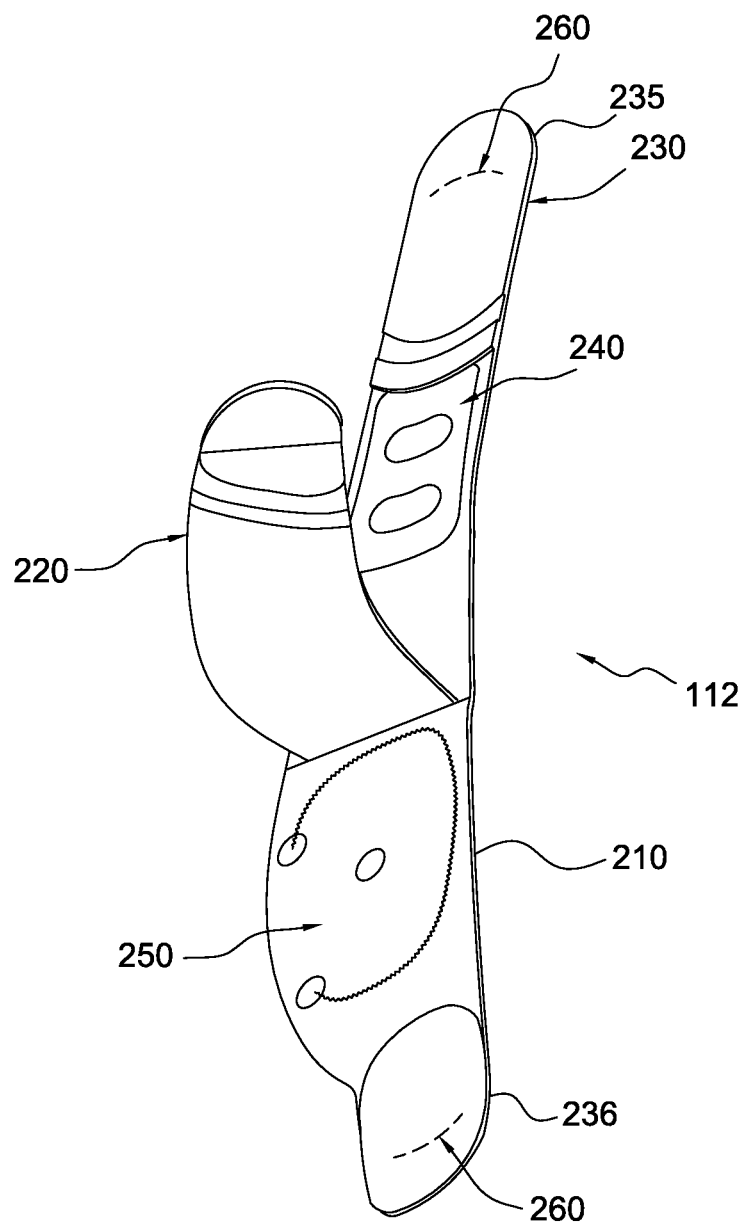
FIG. 2 is a detailed perspective view of the pelvic engaging part belonging to the soft-good assembly of the hip orthosis in FIG. 1B.

An embodiment of the pelvic strap assembly 112 is illustrated in FIG. 2. According to this embodiment, the pelvic strap assembly 112 includes an outer strap 220 generally provided in the center of the pelvic strap assembly 112 to facilitate tightening of the orthosis about the pelvis of the user. Preferably, the outer strap 220 is foldable along a panel portion 210 adapted to receive the hip plate or a panel extension 230. The outer strap 220 can be secured to the panel portion 210 or the panel extension 230 using fastening members well known in the art, i.e., hook and loop fasteners, straps, buttons, pins, buckles. The pelvic strap assembly 112 defines a pocket 250 adapted to receive the hip plate.

The pelvic strap assembly 112 can be wrapped about a user's torso by first taking first and second end portions 235, 236 and securing these end portions to one another (via suitable fasteners such as hook and loop) so as to position the pelvic strap assembly 112. Suitable pockets 260 may be provided at either of the end portions to allow the user to place fingers or a hand therein rather than requiring grasping of the end portions 235, 236. The outer strap 220 can then be used to tighten over the extension panel to assure that the pelvic strap assembly 112 is secure over the user's waist.

In a variation, the extension panel 230 of the pelvic strap assembly 112 is a molded laminated textile. In one variation of the hip orthosis 100, the extension panel 230 prevents rotating and folding of the pelvic strap assembly 112 by including a stay 240 selectively positioned in the custom molded laminated textile. The hip plate 102 may be located adjacent to or spaced away from the stay 240 and depending from the strut assembly.

The stay 240 can be made from ethylene vinyl acetate (EVA) or similar flexible and resilient material and polyester fabric which is used as a backing layer. The stay 240 provides support for the soft good material of the pelvic strap assembly 112 while having sufficient flexibility to tighten the brace when the hip orthosis 100 is worn.

FIGS. 3A-3D disclose an exemplary process for manufacturing the extension panel 230 using a heat press process. According to this method, a top plate having a protruding shape in the shape of a textile material is initially clamped to the top side of a heat press. A bottom plate 312 is then clamped to the bottom side of the heat press and has a recess 314 in a shape to fit the textile material. The different layers are then layered in the recess of the bottom plate in a predetermined order.

Figure 3A:
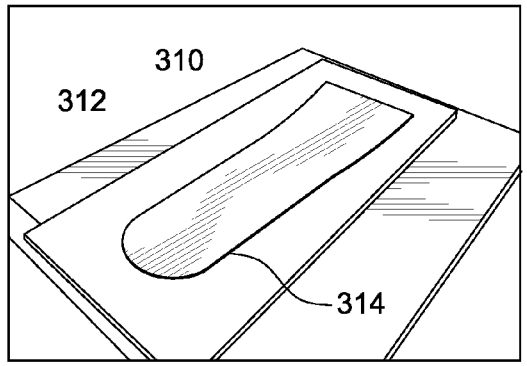
FIGS. 3A-3D are schematic views showing steps for assembling for preparing a textile laminate for use in the pelvic engaging part of FIG. 2.
Figure 3B:
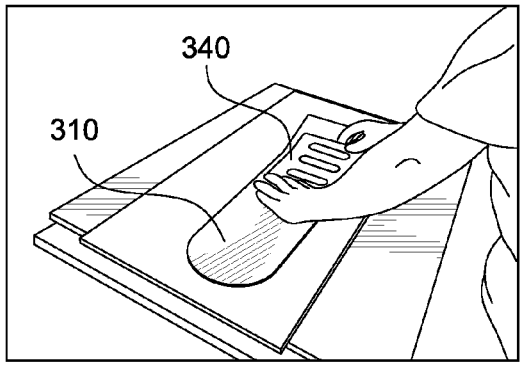

As seen in FIG. 3A, the layering occurs by first placing a first, bottom textile layer 310 in the recess of the bottom plate. Next, as seen in FIG. 3B, a polymeric stay 340 is placed in a pre-determined and preselected area on the first textile layer 310.

The selection of the stay 340 is determined by the specific functionality that is to be accomplished. According to one variation, the stay 240 can be positioned along an end of the extension panel 230 to prevent rotation and folding of the extension panel 230.

Figure 3C:
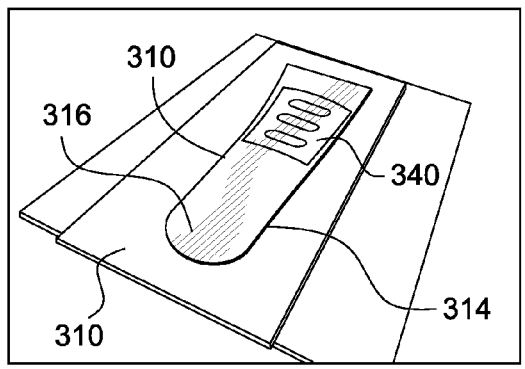
Figure 3D:
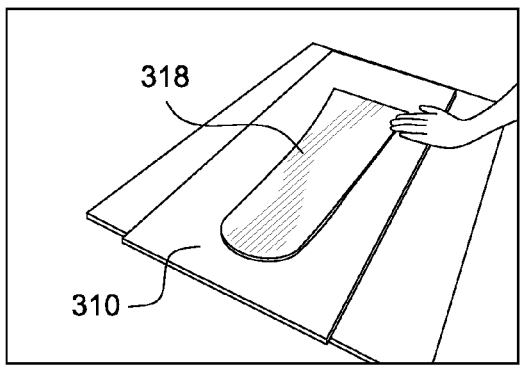

As seen in FIG. 3C, after the stay 340 is positioned in the preselected position, an adhesive layer 316 is placed over the stay and the textile bottom layer. Finally, as seen in FIG. 3D, a second, top textile layer 318 is placed over the combined structure.

The heat press is then heated and pressed together by clamping, pressing, or similar means of applying pressure. The heating of the press effectively melts the adhesive to bind the layers together with the positioned stay 340 to form the extension panel 230.

The stay is a shaped piece of polymeric material and is placed between layers of textile, such as Lycra and a layer of foam. The layers are adhered together during lamination with an adhesive, such as PELLON. The lamination is carried out by layering the textile layers' polymeric material before heating and pressing the layers together. The method is not limited to using polymeric materials, but may employ metal or composite stays.

In conventional textile production, such as lamination, there is typically an equal area of textile, sheet material and textile. This causes the end material to have similar properties over the entire area. Through this method, custom-made shapes made from a polymeric material are preferably used, however it is also envisioned to use materials such as metals and composites for the stay. This method is advantageous in that it is possible to place the stay in localized areas of the laminated textile thereby reducing the overall effect on the user. This makes it possible to a larger degree control the effect of the inserted part.

If the stay is arranged to overlap the spine, then the material selection is made so that the stay is sufficiently soft to avoid any major disturbances. For example, the stay may be 1.5 mm, and selected on to as a softer material over the standard material properties of a polyethylene sheet having a thickness of 1 mm. The thicker stay of 1.5 mm was found to improve the lamination process over a thinner yet harder material and thickness.

The method for manufacturing the extension panel can also be used in any of the other components of the hip orthosis so as to provide reinforcement to various portions of the soft-good components of the hip orthosis. Additionally, the custom molded textile provides the seamless insertion of a stay in a textile product to reduce the risk of external edges or bindings that can irritate the skin. This method of inserting the stay reduces the risk of the movement of the stay by having the stay integrated and securely located between the textile layers. Moreover, the extension panel can also be optionally bound with stitching to reinforce the laminated textile material.

It will be understood that this method is not limited to a hip orthosis, but may be extended to a variety of applications of articles, including shoes, apparels, bags, packs, or similar article having edges or bindings that may irritate the skin.

Figure 4A:
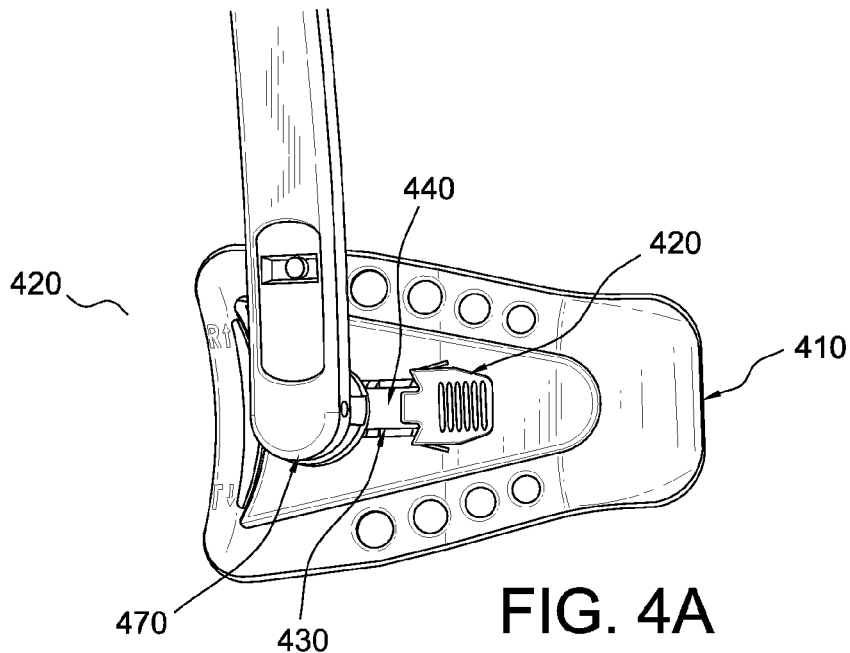
FIGS. 4A-4C are perspective views of an exemplary embodiment of a thigh cuff assembly for the hip orthosis of FIG. 1A.
Figure 4B:
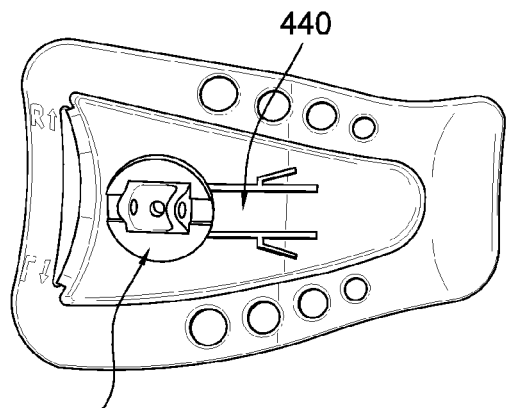
Figure 4C:
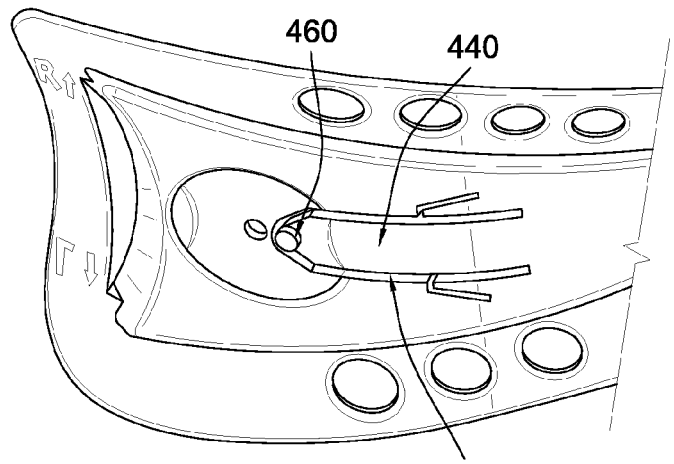

FIGS. 4A-4C illustrate an embodiment of a thigh cuff assembly 410. The thigh cuff assembly 410 can be attached to the user's leg by using a strap capable of being wrapped around the user's thigh, or a lower thigh bandage made from spandex, nylon, or other similar material or combinations thereof.

In the embodiment shown in FIG. 4A, the thigh cuff assembly 410 is capable of pivoting about an axis by a rotational mechanism to allow the repositioning of the spring rod between a right side/hip assembly and a left side/hip assembly. This is accomplished by first disengaging a button lock 420 located along tracks 430 on the outer surface of the thigh cuff assembly 410.

As illustrated in FIG. 4C, once the button lock 420 is released, the thigh cuff assembly 410 is additionally provided with a depressible flange 440 engaging a locking mechanism 450. When the flange 440 is depressed, the lock 460 moves out of its locked position in the locking mechanism 450, wherein the locked position, the lock 460 keeps a rotational mechanism 470 fixed to prevent rotation.

Once the lock 460 is moved from the locked position, the rotational mechanism 470 is released and allowed to freely rotate 360 degrees. When the thigh cuff assembly 410 is rotated about 180 degrees, i.e., the thigh cuff is repositioned from a right side/hip assembly to a left side/hip assembly, the depressible flange 440, which is made from a flexible material, returns to its unloaded state. In other words, the depressible flange 440 can automatically place the lock 460 back into the locked position in the locking mechanism 450 when properly positioned.

Figure 5A:
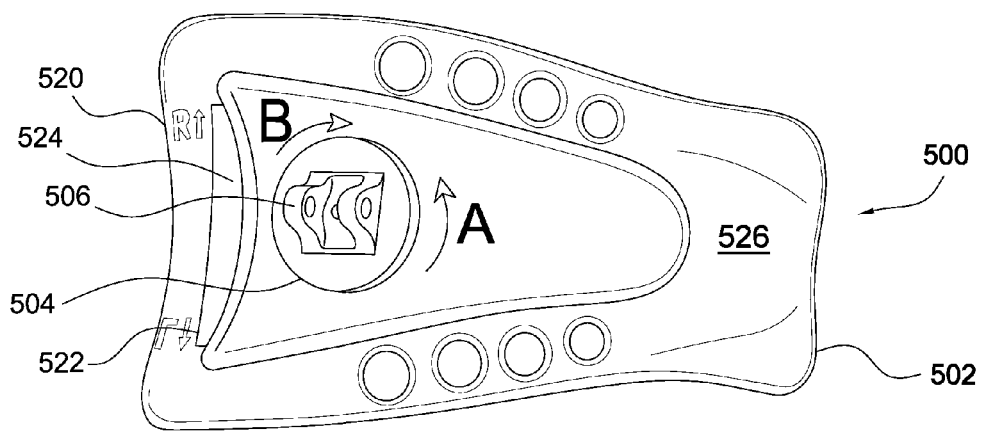
FIGS. 5A-5C are perspective views showing a variation of the thigh cuff assembly according to the hip orthosis of FIGS. 4A-4C.
Figures 5B, 5C:
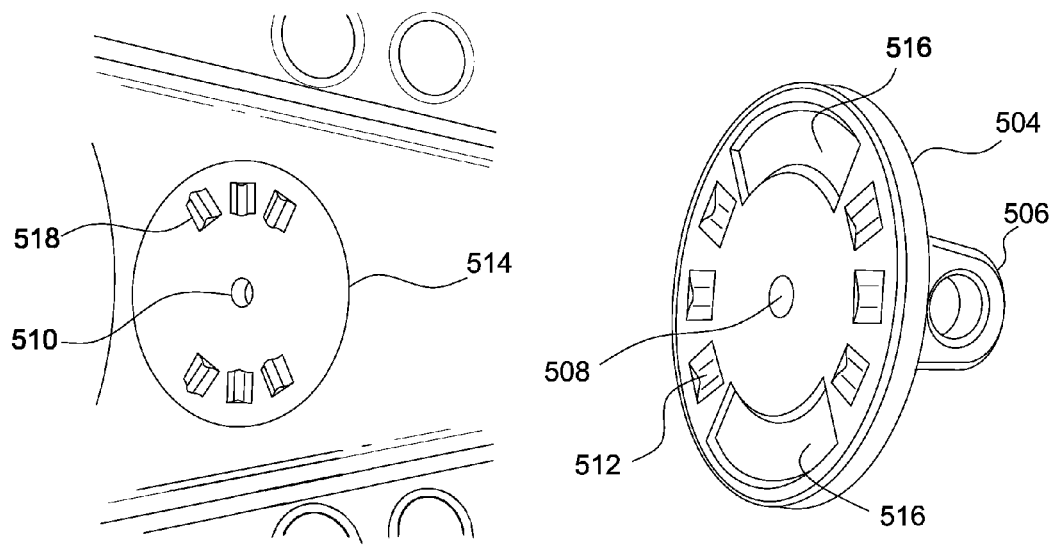

FIGS. 5A-5C illustrate a variation of a thigh cuff assembly 500. According to this variation, the thigh cuff assembly 500 includes a shell 502 adapted to secure to the thigh of the user. A mounting clip 504 is rotatably secured to the shell 502 to allow for the thigh cuff assembly to be adapted for either right or left legs, as indicated by indicia 520, 522. The clip 504 includes a bracket 506 for pivotally securing to the spring rod.

The clip 504 rotates about an aperture 508 formed generally centrally therethrough, and corresponding to aperture 510 formed on the shell 502, with an appropriate fastener securing the clip 504 to the shell 502. The clip 504 defines a plurality of recesses 512 arranged in an arcuate pattern and are located on opposed sides of the clip on a surface facing the shell 502. The clip 504 also defines upper and lower elongate, arcuate recesses 516 corresponding to right or left configurations of the clip 504. The shell 502 defines a plurality of protrusions 518 arranged in arcuate, upper and lower patterns and generally corresponding in location to the elongate recesses 516 when the clip is configured in right or left configurations.

The protrusions 518 serve as semi-rotational brakes to prevent the clip from freely rotating, however some free movement is allowed by the combination of the recesses 512, 516 and the protrusions or semi-rotational brakes 518. The clip 504 can rotate in either rotational directions A, B so as to adjust relative to the shell 502 for adaptation of the hip orthosis in either right or left leg configurations.

When fitting the hip orthosis on the user, the lower thigh cuff assembly is to have a longer portion 526 of the shell 502 positioned toward the anterior aspect of the user's leg. The longer portion 526 is on a first side of the mounting clip region 514, and thus the strut assembly, and is in contrast to a shorter portion 524 on a second side of the mounting clip region 514. The orientation of the cuff depends on whether the brace is being fitted for a right or left hip. The user or clinician fitting the brace can refer to the indicia to assure proper orientation and assembly of the lower thigh cuff.

FIGS. 6A-6D illustrate another embodiment of a thigh cuff assembly 600 for use with the hip orthosis according to FIGS. 1A-1C. In many orthoses, certain cuff assemblies are found to be difficult to reach, particularly for infirm users, complicated to strap, and lack abilities for sizing changes. At least in a hip orthosis, a thigh cuff assembly may have an abduction force in a spring member that makes it difficult to don and difficult to achieve a desired level of tightness.

According to the embodiment of FIGS. 6A-6D, the thigh cuff assembly 600 includes a trimmable cuff 602 secured to a leg strut or spring assembly 604, as discussed above in reference to the hip orthosis, and further includes a tensioning device 606 on a first side 625 of the spring assembly and adapted for adjusting the tension and therefore tightness of the thigh cuff assembly 600 on the user's leg. The tensioning device 606 may be a dial tensioning device coupled to a cable assembly 608 attached to a strap 612, and permits incremental adjustment of the strap 612 relative to the cuff 602. A suitable cover 610 may be provided to at least cover the cable assembly and at least part of the thigh cuff, and has cut-outs 620 for providing access to the tensioning device 606.

A first end of the strap 612 is secured to a cable guide 628 which includes a channel 630 for receiving the cable assembly. As a first end of the strap 612 secures to the cable assembly 608, a second end of the strap 612 includes a bracket 614 and attachment element 616 which is adapted to secure to an opening 632 formed by the cuff 602 on a second side 626 of the spring assembly 604. The bracket 614 may be removed from the opening 632 to thereby allow for quick decoupling of the second strap end from the cuff.

By securing the bracket 614 to the cuff 602, the thigh cuff assembly forms a circumferential cuff assembly for firmly securing to the leg of a user. The tensioning device permits the user to easily grasp and adjust the strap, and thus adjust the tension in the strap despite the abduction force in the spring assembly. Only one hand is needed once the strap bracket is secured to the cuff. Moreover, the cuff is trimmable, and is preferably formed from a trimmable polymeric material so as to allow for customization of the cuff.

The tensioning device may be configured in any manner known to one having ordinary skill in the art. An example of various tensioning devices may be found in U.S. patent application Ser. No. 12/466,597, filed on May 15, 2009, and incorporated herein by reference. An example of brackets and straps may be found in U.S. Pat. No. 7,198,610, granted on Dec. 21, 2005, and incorporated herein by reference.

The strut or spring assembly 604 may be pivotally secured to the cuff 602 by pivoting connection formed of a protrusion 622 formed on the strut or spring assembly and a bracket 624 formed by the cuff. Of course, the strut or spring assembly may be secured in any other manner described in other embodiments discussed herein.

In accordance with a method for adjusting the circumferential configuration of the strap and cuff, the user or clinician incrementally adjusts the tensioning device among a plurality of preselected levels such that a first end of the strap secures to the tensioning device and a second end of the strap couples to the cuff. The combination of the cuff and the strap form a continuous circumferential configuration.

While the foregoing embodiments have been described and shown, it is understood that alternatives and modifications of these embodiments, such as those suggested by others, may be made to fall within the scope of the invention. Moreover, any of the principles described herein may be extended to any other orthopedic devices or other types of articles requiring similar functions of those structural elements described herein.

The invention claimed is:

1. An orthopedic device, comprising:
an elongate and rigid or semirigid strut assembly having a first end portion defining a width;
a hip plate engaging the first end portion of the strut assembly;
an arcuate cuff pivotally secured to the strut assembly at a second end portion of the strut assembly and adapted for a lower thigh, the arcuate cuff having a longer portion and a shorter portion on opposed sides of the strut assembly;
a strap securing to the arcuate cuff and forming an adjustable circumferential configuration therewith; and
a mounting clip attached to the arcuate cuff, the mounting clip coupling to the strut assembly and permitting rotation of the arcuate cuff relative to the strut assembly at a single pivot axis; wherein the mounting clip rotates about an aperture formed centrally therethrough and corresponding to an aperture formed on the arcuate cuff with a fastener securing the mounting clip to the arcuate cuff such that the arcuate cuff is rotatable via the fastener relative to the strut assembly by at least 180 degrees to allow for the arcuate cuff to be adapted for either right or left legs according to indicia provided on the arcuate cuff, such that the longer portion of the arcuate cuff is adapted for placement over an anterior aspect of a leg in both right and left leg configurations.

2. The orthopedic device according to claim 1, further comprising a tensioning device mounted on the arcuate cuff and coupled to the strap, the tensioning device arranged for incrementally adjusting a circumference of the circumferential configuration.

3. The orthopedic device according to claim 2, further comprising a covering, the tensioning device having a cable coupling the tensioning device to the strap, the covering extending over the cable and the arcuate cuff.

4. The orthopedic device according to claim 2, wherein a first end of the strap secures to the tensioning device and a second end of the strap couples to the arcuate cuff.

* * * * *